(12) United States Patent
Natesan et al.

(10) Patent No.: US 12,350,453 B2
(45) Date of Patent: Jul. 8, 2025

(54) CATHETER SYSTEM FACILITATING BLOOD FLASHBACK VISUALIZATION

(71) Applicant: Becton, Dickinson and Company, Franklin Lakes, NJ (US)

(72) Inventors: Mohankumar Natesan, Singapore (SG); Jithendra Kumar Sathyanarayana Naidu, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 155 days.

(21) Appl. No.: 17/337,200

(22) Filed: Jun. 2, 2021

(65) Prior Publication Data

US 2021/0386977 A1    Dec. 16, 2021

Related U.S. Application Data

(60) Provisional application No. 63/037,354, filed on Jun. 10, 2020.

(51) Int. Cl.
*A61M 25/06* (2006.01)
*A61M 5/34* (2006.01)
(Continued)

(52) U.S. Cl.
CPC .......... *A61M 25/0693* (2013.01); *A61M 5/34* (2013.01); *A61M 25/0097* (2013.01); *A61M 25/0631* (2013.01); *A61M 2039/205* (2013.01)

(58) Field of Classification Search
CPC .......... A61M 25/0693; A61M 25/0097; A61M 25/0606; A61M 39/20; A61M 2039/205;
(Continued)

(56) References Cited

U.S. PATENT DOCUMENTS 4,917,671 A    4/1990  Chang
5,032,116 A *  7/1991  Peterson ........... A61M 25/0693
                                                   604/168.01

(Continued)

FOREIGN PATENT DOCUMENTS

AT    98882 T    1/1994
AT    108671 T   8/1994
(Continued)

*Primary Examiner* — William R Carpenter
*Assistant Examiner* — Robert F Allen
(74) *Attorney, Agent, or Firm* — Kirton McConkie; Whitney Blair; Kevin Stinger

(57) ABSTRACT

A catheter system may include a catheter assembly, which may include a catheter adapter and a catheter. The catheter system may also include a needle assembly, which may include a needle hub and an introducer needle. A proximal end of the introducer needle may be secured within the needle hub, and a distal end of the introducer needle may extend beyond a distal end of the catheter. The catheter system may include a vent plug. A distal end of the vent plug may include a male luer adapter, which may include a cannula and a collar surrounding the cannula. The cannula may include a cavity to receive blood flowing proximally through the introducer needle. A proximal end of the cavity may be formed by a wall extending across the cannula and disposed within the needle hub. The cannula may be inserted into the proximal end of the needle hub.

16 Claims, 3 Drawing Sheets

(51) Int. Cl.
*A61M 25/00* (2006.01)
*A61M 39/20* (2006.01)

(58) Field of Classification Search
CPC ............ A61M 2205/7536; A61M 5/34; A61M 2205/583; A61M 25/065; A61M 2025/0089; A61B 5/15; A61B 5/150007; A61B 5/150015; A61B 5/15003; A61B 5/150213; A61B 5/150992
See application file for complete search history.

(56) References Cited

U.S. PATENT DOCUMENTS

| | | | | |
|---|---|---|---|---|
| 5,066,284 | A | * | 11/1991 | Mersch ............ A61M 25/0693 604/168.01 |
| 5,437,647 | A | * | 8/1995 | Firth ..................... A61B 5/411 604/110 |
| 5,501,671 | A | | 3/1996 | Rosen et al. |
| 5,624,400 | A | * | 4/1997 | Firth ................ A61B 5/150641 604/110 |
| 5,820,596 | A | * | 10/1998 | Rosen ............... A61M 25/0693 604/168.01 |
| 5,980,492 | A | | 11/1999 | Rosen et al. |
| 5,984,895 | A | * | 11/1999 | Padilla .............. A61M 25/0693 604/168.01 |
| 6,156,010 | A | * | 12/2000 | Kuracina .......... A61M 25/0693 600/580 |
| 2002/0004647 | A1 | * | 1/2002 | Leong ................ A61B 5/15003 604/168.01 |
| 2002/0055715 | A1 | * | 5/2002 | Young ............... A61M 25/0693 600/584 |
| 2008/0147009 | A1 | * | 6/2008 | Nilsson ............. A61M 25/0606 604/164.08 |
| 2008/0262430 | A1 | * | 10/2008 | Anderson ............. A61M 25/09 604/165.01 |
| 2015/0173663 | A1 | * | 6/2015 | Teoh ................ A61B 5/150274 600/576 |
| 2015/0306351 | A1 | | 10/2015 | Bornhoft |
| 2017/0120017 | A1 | * | 5/2017 | Burkholz .......... A61M 25/0606 |
| 2018/0318557 | A1 | * | 11/2018 | Burkholz ............. A61M 39/10 |
| 2018/0344985 | A1 | * | 12/2018 | Shah ................. A61M 25/0606 |
| 2019/0159804 | A1 | * | 5/2019 | Cameron ............ A61M 5/3286 |
| 2020/0008898 | A1 | * | 1/2020 | Rousche ............ A61M 5/16813 |
| 2020/0016376 | A1 | * | 1/2020 | Natesan ........... A61M 25/0606 |
| 2020/0222671 | A1 | | 7/2020 | Burkholz et al. |
| 2021/0068729 | A1 | * | 3/2021 | Kunardi ........... A61B 5/150213 |
| 2021/0077786 | A1 | * | 3/2021 | Wang ................ A61M 25/0625 |
| 2022/0331562 | A1 | * | 10/2022 | Jaros ................. A61M 25/0618 |
| 2024/0268798 | A1 | * | 8/2024 | Kopp ................. A61B 10/0045 |
| 2025/0032758 | A1 | * | 1/2025 | Koehler ............ A61M 25/0693 |

FOREIGN PATENT DOCUMENTS

| | | |
|---|---|---|
| AU | 2015250121 A1 | 11/2016 |
| AU | 2018261521 A1 | 4/2019 |
| AU | 2019302343 A1 | 3/2021 |
| BR | 112016024689 A2 | 8/2017 |
| BR | 112019022075 A2 | 5/2020 |
| BR | 112021000142 A2 | 4/2021 |
| CA | 2015834 A1 | 11/1990 |
| CA | 1307431 C | 9/1992 |
| CA | 2134301 A1 | 5/1995 |
| CA | 2946403 A1 | 10/2015 |
| CA | 3038151 A1 | 11/2018 |
| CA | 3105016 A1 | 1/2020 |
| CN | 204931804 U | 1/2016 |
| CN | 106456941 A | 2/2017 |
| CN | 106620940 A | 5/2017 |
| CN | 206687973 U | 12/2017 |
| CN | 108785829 A | 11/2018 |
| CN | 208785540 U | 4/2019 |
| CN | 112402734 A | 2/2021 |
| CN | 112512617 A | 3/2021 |
| CN | 113730767 A | 12/2021 |
| DE | 68911615 T2 | 5/1994 |
| DE | 69010758 T2 | 10/1994 |
| EP | 353905 | 2/1990 |
| EP | 397038 | 11/1990 |
| EP | 0655259 A2 | 5/1995 |
| EP | 3134159 A1 | 3/2017 |
| EP | 3368130 A1 | 9/2018 |
| EP | 3618912 A2 | 3/2020 |
| EP | 3669924 A1 | 6/2020 |
| EP | 3820556 A1 | 5/2021 |
| ES | 2056292 T3 | 10/1994 |
| ES | 2793279 T3 | 11/2020 |
| IE | 901461 A1 | 2/1991 |
| JP | H031878 A | 1/1991 |
| JP | 2017515555 A | 6/2017 |
| JP | 2019536540 A | 12/2019 |
| JP | 6785963 B2 | 11/2020 |
| JP | 2021531083 A | 11/2021 |
| KR | 20210030363 A | 3/2021 |
| SG | 11201608718 U | 10/2016 |
| SG | 11201803067 W | 5/2018 |
| SG | 11201902690 Y | 11/2019 |
| SG | 11202100017 U | 1/2021 |
| SG | 10202108754 | 9/2021 |
| WO | 2015164131 A1 | 10/2015 |
| WO | 2017074679 A1 | 5/2017 |
| WO | 2018204636 A2 | 11/2018 |
| WO | 2020013947 A1 | 1/2020 |

\* cited by examiner

CATHETER SYSTEM FACILITATING BLOOD FLASHBACK VISUALIZATION

RELATED APPLICATIONS

This application claims benefit of U.S. Provisional Patent Application No. 63/037,354, filed on Jun. 10, 2020, entitled CATHETER SYSTEM FACILITATING BLOOD FLASHBACK VISUALIZATION, which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous catheter ("PIVC"). As its name implies, the over-the-needle PIVC may be mounted over an introducer needle having a sharp distal tip. The PIVC and the introducer needle may be assembled so that the distal tip of the introducer needle extends beyond the distal tip of the PIVC with the bevel of the needle facing up away from skin of the patient. The PIVC and the introducer needle are generally inserted at a shallow angle through the skin into vasculature of the patient.

In order to verify proper placement of the introducer needle and/or the PIVC in the blood vessel, a user generally confirms that there is flashback of blood within a catheter system that includes the PIVC. The user visualizes the flashback of blood within the catheter system to determine the introducer needle is within the vasculature. Once placement of the needle has been confirmed, the user may temporarily occlude flow in the vasculature and remove the introducer needle, leaving the PIVC in place for future blood withdrawal and/or fluid infusion. The PIVC assembly may be coupled with an extension set, which may allow coupling of an infusion or blood withdrawal device at a location removed from an insertion site of the PIVC.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access systems and related devices and methods. In some embodiments, a catheter system may include a catheter assembly, which may include a catheter adapter. In some embodiments, the catheter adapter may include a distal end and a proximal end. In some embodiments, the catheter assembly may include a catheter extending distally from the distal end of the catheter adapter. In some embodiments, the catheter may include a distal end and a proximal end. In some embodiments, the catheter may include a peripheral intravenous catheter (PIVC), a peripherally-inserted central catheter, or a midline catheter.

In some embodiments, the catheter system may also include a needle assembly, which may include a needle hub. In some embodiments, the needle hub may include a distal end and a proximal end. In some embodiments, the needle assembly may include an introducer needle, which may include a distal end and a proximal end. In some embodiments, the proximal end of the introducer needle may be secured within the needle hub. In some embodiments, the distal end of the introducer needle may be sharp and may extend beyond a distal end of the catheter.

In some embodiments, the catheter system may include a vent plug, which may include a distal end and a proximal end. In some embodiments, a distal end of the vent plug may include a male luer adapter, which may include a cannula and a collar surrounding the cannula. In some embodiments, the cannula may include a cavity to receive blood flowing proximally through the introducer needle. In some embodiments, a proximal end of the cavity may be formed by a wall extending across the cannula and disposed within the needle hub. In some embodiments, the cannula may be inserted into proximal end of the needle hub.

In some embodiments, a bottom portion of the cavity may extend distal to the proximal end of the introducer needle. In some embodiments, a portion of the cannula distal to the wall may be semi-annular such that there is a gap oriented above the introducer needle to facilitate visualization of blood exiting the proximal end of the introducer needle by a user. In some embodiments, the wall may include a vent membrane, which may pass air but not blood.

In some embodiments, in response to insertion of the introducer needle into vasculature of a patient by the user, blood may flow proximally through the introducer needle and into the cavity. In some embodiments, in response to blood flowing proximally through the introducer needle, air may move proximally through the vent membrane and/or out of the catheter system via another suitable pathway. In some embodiments, the catheter system may facilitate visualization of the blood by the user. In some embodiments, in response to visualization of the blood by the user, the user may remove the needle assembly from the catheter assembly, which may remain positioned within the vasculature for future blood withdrawal and/or fluid infusion.

In some embodiments, the catheter system may include a cap coupled to the proximal end of the vent plug. In some embodiments, the wall may be spaced apart from a proximal end of the cap. In some embodiments, the vent plug may include an annular channel, which may extend from the wall to the proximal end of the cap. In some embodiments, the cap may include another male luer. In some embodiments, the other male luer may include another cannula and another collar surrounding the other cannula. In some embodiments, the proximal end of the cap may include the other cannula.

In some embodiments, a thickness of the needle hub may allow visualization of blood that has exited the proximal end of the introducer needle. In some embodiments, the needle hub may include an annular wall. In some embodiments, a top portion of the annular wall may include a pocket to reduce a thickness of the top portion of the annular wall. In some embodiments, a portion of the cannula distal to the wall is semi-annular such that there is a gap oriented above the introducer needle to facilitate visualization of blood exiting the proximal end of the introducer needle by the user.

It is to be understood that both the foregoing general description and the following detailed description are examples and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1:
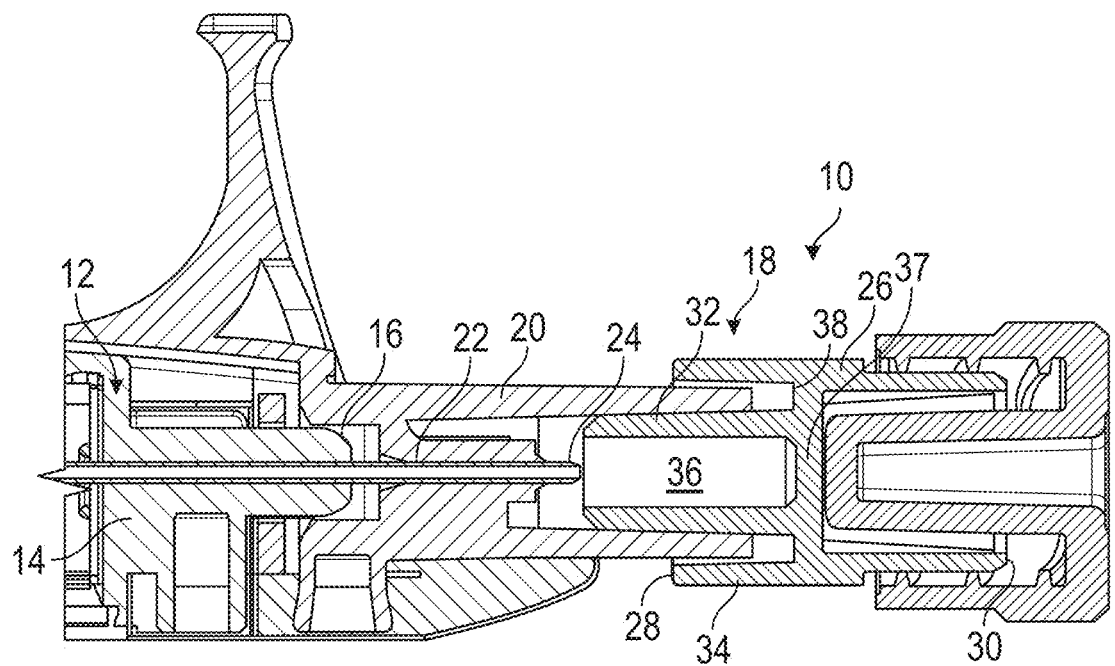
FIG. 1 is a cross-sectional view of a portion of a prior art catheter system, according to some embodiments.

The term "proximal" will refer to the portion of a structure closer to a user, while the term "distal" refers to the portion further from the user. Referring now to FIG. 1, a portion of a prior art catheter system 10 is illustrated. The prior art catheter system 10 includes a catheter assembly 12. The catheter assembly 12 includes a catheter adapter 14. The catheter adapter 14 includes a proximal end 16. The prior art catheter system 10 includes a needle assembly 18, which may include a needle hub 20. The needle assembly 18 includes an introducer needle 22. The introducer needle 22 includes a proximal end 24 secured within the needle hub 20.

The prior art catheter system 10 includes a vent plug 26, which includes a distal end 28 and a proximal end 30. The distal end 28 of the vent plug 26 includes a male luer adapter, which includes a cannula 32 and a collar 34 surrounding the cannula 32. The cannula 32 may include a cavity 36 to receive blood flowing proximally through the introducer needle 22. A proximal end of the cavity 36 is formed by a wall 37, which is disposed outside the needle hub 20. In some embodiments, the cannula 32 is inserted into a proximal end 38 of the needle hub 20.

Figure 2A:
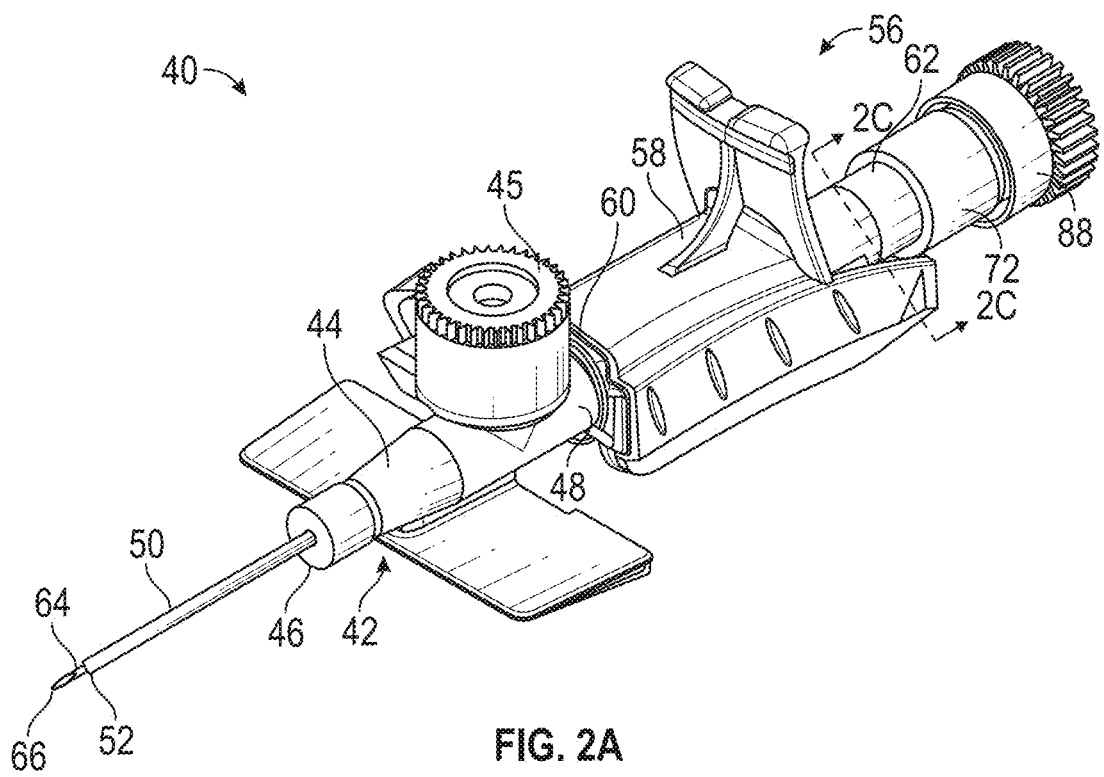
FIG. 2A is an upper perspective view of an example catheter system, according to some embodiments.
Figure 2B:
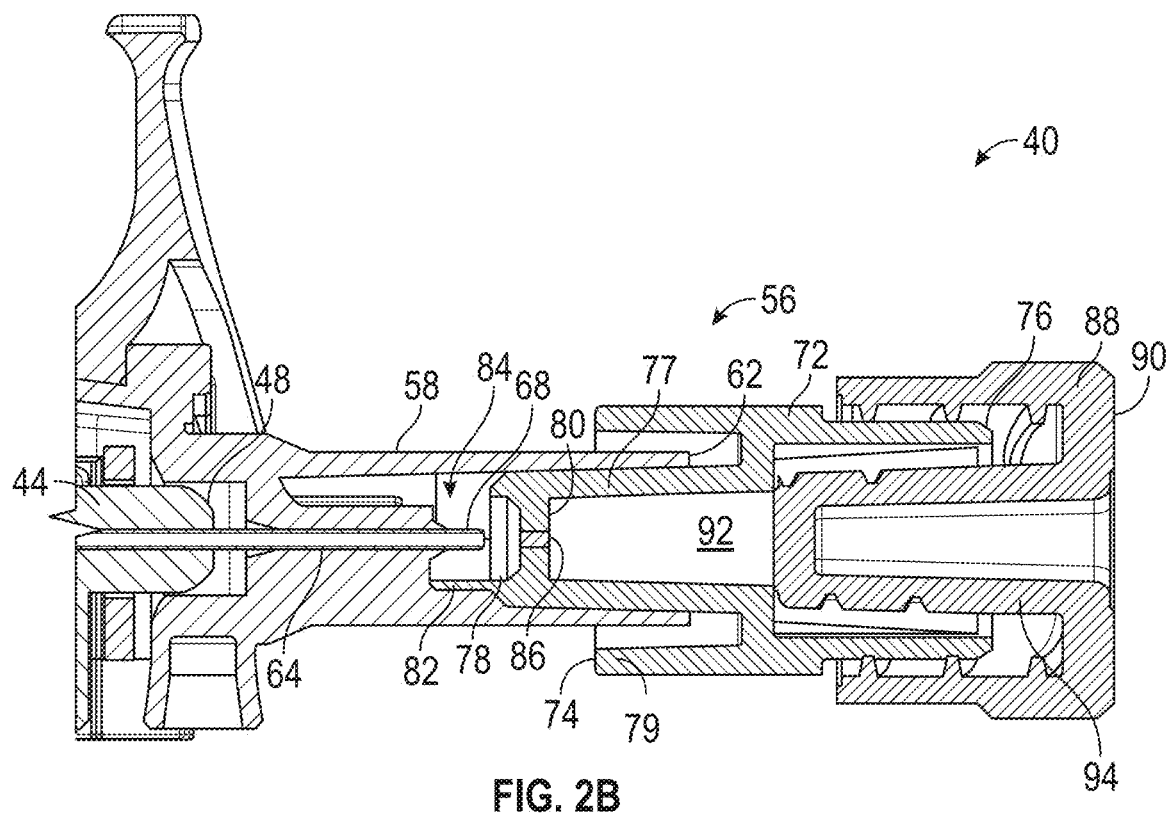
FIG. 2B is a cross-sectional view of a portion of the catheter system of FIG. 2A, according to some embodiments.
Figure 2C:
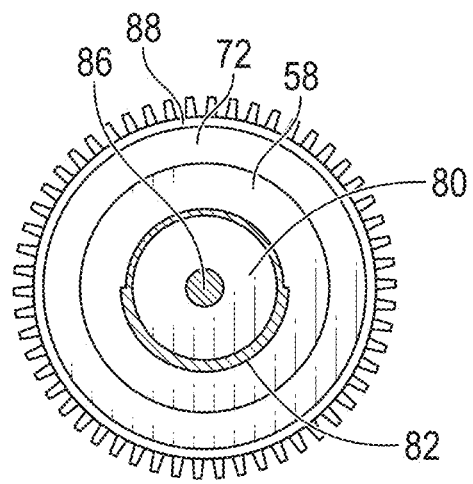
FIG. 2C is a transverse cross-sectional view of the catheter system of FIG. 2A along the line 2C-2C of FIG. 2A, according to some embodiments.

Referring now to FIGS. 2A-2B, in some embodiments, a catheter system 40 may include a catheter assembly 42, which may include a catheter adapter 44. In some embodiments, the catheter adapter 44 may include a distal end 46 and a proximal end 48. In some embodiments, the catheter adapter 44 may include a port disposed between the distal end 46 and the proximal end 48. In some embodiments, the port may be closed with a cap 45, as illustrated, for example, in FIG. 2A.

In some embodiments, the catheter assembly 42 may include a catheter 50 extending distally from the distal end 46 of the catheter adapter 44. In some embodiments, the catheter 50 may include a distal end 52 and a proximal end. In some embodiments, the catheter 50 may include a peripheral intravenous catheter (PIVC), a peripherally-inserted central catheter, or a midline catheter. In some embodiments, the catheter system 40 may include a BD VENFLON™ Pro Safety catheter system available from Becton, Dickinson & Company of Franklin Lakes, New Jersey, or another suitable catheter system.

In some embodiments, the catheter system 40 may also include a needle assembly 56, which may include a needle hub 58. In some embodiments, the needle hub 58 may include a distal end 60 and a proximal end 62. In some embodiments, the needle assembly 56 may include an introducer needle 64, which may include a distal end 66 and a proximal end 68. In some embodiments, the proximal end 68 of the introducer needle 64 may be secured within the needle hub 58. In some embodiments, the distal end 66 of the introducer needle 64 be sharp and may extend beyond the distal end 52 of the catheter 50. In some embodiments, a thickness of a wall of the introducer needle 64 may be less than a thickness of a wall of the introducer needle 22 of the prior art catheter system 10, which may facilitate rapid flow of blood proximally through the introducer needle 64 and visualization within the cavity 78

In some embodiments, the catheter system 40 may include a vent plug 72, which may include a distal end 74 and a proximal end 76. In some embodiments, a distal end 74 of the vent plug 72 may include a male luer adapter, which may include a cannula 77 and a collar 79 surrounding the cannula 77. In some embodiments, the cannula 77 may include a cavity 78 to receive blood flowing proximally through the introducer needle 64. In some embodiments, a proximal end of the cavity 78 may be formed by a wall 80 extending across the cannula 77 and disposed within the needle hub 58. In some embodiments, the cannula 77 may be inserted into proximal end 62 of the needle hub 58.

In some embodiments, a length of the cavity 78 aligned with a longitudinal axis of the introducer needle 64 may be less than a length of the cavity 36 of the needle hub 20 of the prior art catheter system 10. Additionally or alternatively, in some embodiments, a depth of the cavity 78 perpendicular to a longitudinal axis of the introducer needle 64 may be less than a depth of the cavity 36 of the needle hub 20 of the prior art catheter system 10. Thus, in some embodiments, the blood flowing through the introducer needle 64 from the patient may be visualized more quickly in the catheter system 40.

In some embodiments, a portion 82 of the cannula 77 distal to the wall 80 may be semi-annular such that there is a gap 84 oriented above the introducer needle 64 to facilitate visualization of blood exiting the proximal end 68 of the introducer needle 64 by a user. In some embodiments, the portion 82 of the cannula 77 may be disposed towards a bottom of the vent plug 72 and the catheter system 40. As used in the present disclosure, a top of a particular structure may face away from skin of a patient, while a bottom of a particular structure may face toward from the skin of the patient. In some embodiments, the portion 82 of the cannula 77 may extend distal to the proximal end 68 of the introducer needle 64.

In some embodiments, the wall 80 may include a vent membrane 86, which may pass air but not blood. In some embodiments, in response to insertion of the introducer needle 64 into vasculature of a patient by the user, blood may flow proximally through the introducer needle 64 and into the cavity 78. In some embodiments, in response to blood flowing proximally through the introducer needle 64 and the cap 88 being removed, air may move proximally through the vent membrane 86 and out of the catheter system 40. In some embodiments, the catheter system 40 may facilitate visualization of the blood by the user. In some embodiments, in response to visualization of the blood by the user, the user may remove the needle assembly 56 from the catheter assembly 42, which may remain positioned within the vasculature for future blood withdrawal and/or fluid infusion.

In some embodiments, the catheter system 40 may include a cap 88 coupled to the proximal end 76 of the vent plug 72. In some embodiments, the wall 80 may be spaced apart from a proximal end 90 of the cap 88. In some embodiments, the vent plug 72 may include an annular channel 92, which may extend from the wall 80 to the distal end of the cap 88. In some embodiments, the cap 88 may include another male luer. In some embodiments, the another male luer may include another cannula 94 and another collar surrounding the another cannula 94. In some embodiments, the proximal end 90 of the cap 88 may include the other cannula 94.

In some embodiments, a thickness of the needle hub 58 may allow visualization of blood that has exited the proximal end of the introducer needle 64. In some embodiments, the thickness of the needle hub 58 may be less than a thickness of the needle hub 20 of the prior art catheter system 10.

Figure 3:
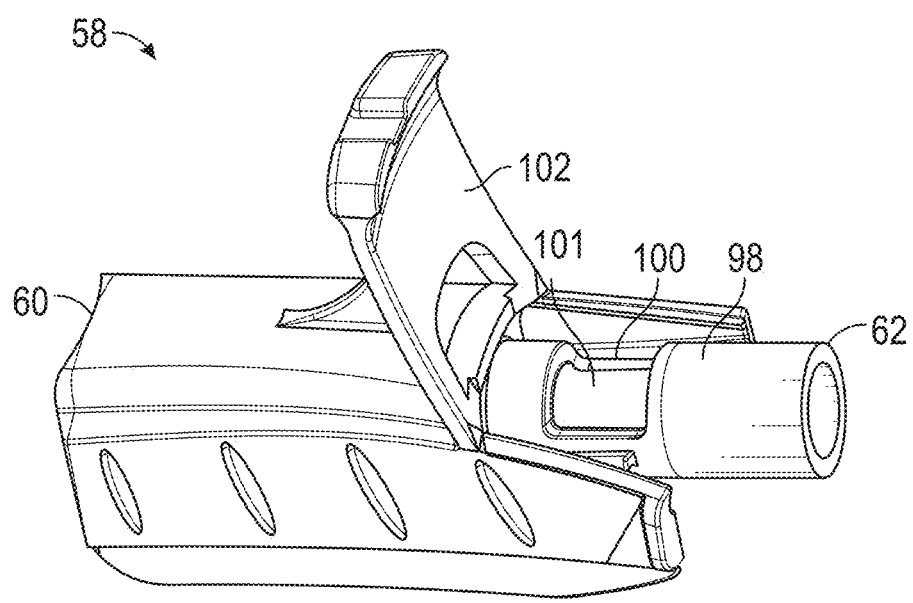
FIG. 3 is an upper perspective view of an example needle hub, according to some embodiments.

Referring now to FIG. 3, in some embodiments, the needle hub 58 may include an annular wall 98. In some embodiments, a top portion of the annular wall 98 may include a pocket 100 to reduce a thickness of the top portion of the annular wall 98, which may facilitate visualization by the user of blood travelling out the proximal end 68 of the introducer needle 64. In some embodiments, the pocket 100 may include a groove or a portion of the annular wall 98 that is cut away or thinned such that the user can see blood within the needle assembly 56 through the annular wall 98. The pocket 100 is not an opening, so blood cannot flow through the pocket 100. The pocket 100 may include a bottom wall 101. In some embodiments, the needle hub 58 may include a push tab 102, which may be generally aligned with the pocket 100.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A catheter system, comprising:
   a catheter assembly, comprising:
   a catheter adapter, comprising a distal end and a proximal end;
   a catheter extending distally from the distal end of the catheter adapter; and
   a needle assembly, comprising:
   a needle hub, comprising a distal end and a proximal end, wherein the needle hub comprises an annular wall and a pocket disposed within a top portion of the annular wall, wherein the pocket comprises a bottom wall extending from a distal end of the pocket to a proximal end of the pocket, wherein blood within the needle hub is visualized through the bottom wall, wherein an outer diameter of the annular wall along an entirety of the bottom wall from the distal end of the pocket to the proximal end of the pocket is uniform and less than an outer diameter of the annular wall immediately distal to and immediately proximal to the pocket, wherein an interior surface of the annular wall at the pocket is configured to contact blood flashback, wherein the pocket is monolithically formed as single unit with the annular wall immediately distal to and immediately proximal to the pocket;
   an introducer needle, comprising a distal end and a proximal end, wherein the proximal end of the introducer needle is secured within the needle hub, wherein the distal end of the introducer needle extends beyond a distal end of the catheter; and
   a vent plug, comprising a distal end and a proximal end, wherein the vent plug comprises a male luer adapter, wherein the male luer adapter comprises a cannula and a collar surrounding the cannula, wherein the cannula comprises a cavity to receive blood flashback flowing proximally through the introducer needle, wherein a proximal end of the cavity is formed by a wall extending across the cannula and disposed within the needle hub, wherein the cannula is inserted into the proximal end of the needle hub, wherein a portion of the wall comprises a vent membrane, wherein the vent membrane is configured to pass air and not blood.

2. The catheter system of claim 1, wherein a bottom portion of the cavity extends distal to the proximal end of the introducer needle.

3. The catheter system of claim 1, wherein the catheter system further comprises a cap coupled to the proximal end of the vent plug, wherein the wall is spaced apart from a proximal end of the cap.

4. The catheter system of claim 3, wherein the vent plug comprises an annular channel extending from the wall to a distal end of the cap.

5. The catheter system of claim 4, wherein the cap comprises another male luer, wherein the another male luer comprises another cannula and another collar surrounding the another cannula, wherein the proximal end of the cap comprises the another cannula.

6. The catheter system of claim 1, wherein a thickness of the needle hub allows visualization of blood that has exited the proximal end of the introducer needle.

7. A catheter system, comprising:
   a catheter assembly, comprising:
   a catheter adapter, comprising a distal end and a proximal end;
   a catheter extending distally from the distal end of the catheter adapter; and
   a needle assembly, comprising:
   a needle hub, comprising a distal end, a proximal end, an annular wall, and a pocket disposed within a top portion of the annular wall, wherein the pocket comprises a bottom wall extending from a distal end of the pocket to a proximal end of the pocket, wherein blood within the needle hub is visualized through the bottom wall, wherein an outer diameter of the annular wall along an entirety of the bottom wall from a distal end of the pocket to a proximal end of the pocket is uniform and less than an outer diameter of the annular wall immediately distal to and immediately proximal to the pocket, wherein an interior surface of the annular wall at the pocket is configured to contact blood flashback, wherein the pocket is monolithically formed as single unit with the annular wall immediately distal to and immediately proximal to the pocket;
   an introducer needle, comprising a distal end and a proximal end, wherein the proximal end of the introducer needle is secured within the needle hub, wherein the distal end of the introducer needle extends beyond a distal end of the catheter; and a vent plug comprising a distal end and a proximal end, wherein the distal end of the vent plug comprises a male luer adapter inserted into the proximal end of the needle hub, wherein the male luer adapter comprises a cannula and a collar surrounding the cannula.

8. The catheter system of claim 7, wherein the cannula comprises a cavity to receive blood flowing proximally through the introducer needle, wherein a proximal end of the cavity is formed by a wall extending across the cannula and disposed within the needle hub, wherein the cannula is inserted into the proximal end of the needle hub.

9. The catheter system of claim 8, wherein a portion of the cannula is distal to the wall and wherein the portion of the cannula is semi-annular such that there is a gap oriented above the introducer needle to facilitate visualization of blood exiting the proximal end of the introducer needle.

10. The catheter system of claim 9, wherein a bottom portion of the cavity extends distal to the proximal end of the introducer needle.

11. The catheter system of claim 8, wherein the wall comprises a vent membrane.

12. The catheter system of claim 8, wherein the catheter system further comprises a cap coupled to the proximal end of the vent plug, wherein the wall is spaced apart from a distal end of the cap.

13. The catheter system of claim 12, wherein the vent plug comprises an annular channel extending from the wall to the distal end of the cap.

14. The catheter system of claim 13, wherein the cap comprises another male luer, wherein the another male luer comprises another cannula and another collar surrounding the another cannula, wherein a proximal end of the cap comprises the another cannula.

15. The catheter system of claim 7, wherein the catheter comprises a peripheral intravenous catheter.

16. The catheter system of claim 7, wherein the pocket is disposed on a top of the needle hub such that the pocket faces away from skin of a patient to facilitate visualization of blood travelling out of the proximal end of the introducer needle.

* * * * *